United States Patent [19]

O'Callaghan et al.

[11] Patent Number: 4,621,081

[45] Date of Patent: * Nov. 4, 1986

[54] CEPHALOSPORIN ANTIBIOTICS

[75] Inventors: Cynthia H. O'Callaghan, Gerrards Cross; Barry E. Ayres, Ickenham; David G. H. Livermore; Christopher E. Newall, both of London; Niall G. Weir, Wembley, all of England

[73] Assignee: Glaxo Group Limited, London, England

[*] Notice: The portion of the term of this patent subsequent to Mar. 12, 2002 has been disclaimed.

[21] Appl. No.: 423,555

[22] Filed: Sep. 27, 1982

Related U.S. Application Data

[60] Continuation of Ser. No. 285,573, Jul. 21, 1981, abandoned, which is a continuation of Ser. No. 176,535, Aug. 8, 1980, abandoned, which is a continuation of Ser. No. 112,205, Jan. 15, 1980, abandoned, which is a division of Ser. No. 42,595, May 25, 1979, abandoned.

[30] Foreign Application Priority Data

| May 26, 1978 | [GB] | United Kingdom | 23041/78 |
| May 26, 1978 | [GB] | United Kingdom | 23042/78 |
| Oct. 27, 1978 | [GB] | United Kingdom | 42166/78 |
| Oct. 27, 1978 | [GB] | United Kingdom | 42196/78 |

[51] Int. Cl.$^4$ .............. C07D 501/36; A61K 31/545
[52] U.S. Cl. .................. 514/206; 540/225; 540/227
[58] Field of Search ............ 544/26, 27, 25; 424/246

[56] References Cited

U.S. PATENT DOCUMENTS

| 4,095,021 | 6/1978 | Bradshaw et al. | 544/25 |
| 4,237,128 | 12/1980 | Cimarusti et al. | 544/27 |
| 4,278,793 | 7/1981 | Dürckheimer et al. | 544/25 |
| 4,315,005 | 2/1982 | Ayres et al. | 544/25 |
| 4,504,477 | 3/1985 | O'Callaghan et al. | 544/25 |

Primary Examiner—Nicholas S. Rizzo
Attorney, Agent, or Firm—Bacon & Thomas

[57] ABSTRACT

Cephalosporin antibiotics of general formula:

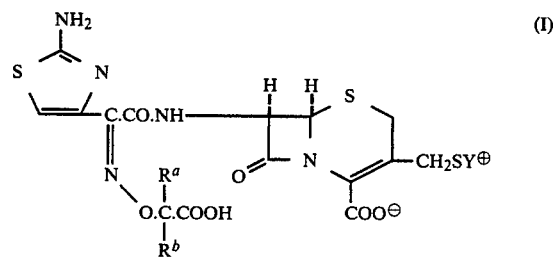

(wherein $R^a$ and $R^b$, which may be the same or different, each represent a $C_{1-4}$ alkyl group or $R^a$ and $R^b$ together with the carbon atom to which they are attached form a $C_{3-7}$ cycloalkylidene group, and $Y^\oplus$ represents a C-linked 5- or 6-membered heterocyclic ring containing at least one $C_{1-4}$ alkyl-substituted quaternary nitrogen atom, which ring may also contain one or more sulphur atoms) exhibit broad spectrum antibiotic activity, the activity being unusually high against gram-negative organisms such as strains of Pseudomonas organisms.

A particular antibiotic compound of formula (I) possessing excellent antibacterial activity against strains of Pseudomonas organisms, as well as other valuable therapeutic properties, is (6R,7R)-7-[(Z)-2-(2-aminothiazol-4-yl)-2-(1-carboxycyclobut-1-oxyimino)acetamido]-3-[(1-methylpyridinium-4-yl)-thiomethyl]ceph-3-em-4-carboxylate. The invention also includes the non-toxic salts and non-toxic metabolically labile esters of compounds of formula (I). Also described are compositions containing the antibiotics of the invention and processes for the preparation of the antibiotics.

13 Claims, No Drawings

CEPHALOSPORIN ANTIBIOTICS

This application is a continuation, of application Ser. No. 285,573, filed 07/21/81, now aband. which is a continuation of Ser. No. 176,535, filed 08/08/80, now aband. which is a continuation of Ser. No. 112,205, filed 01/15/80, now aband. which is a divisional of Ser. No. 042,595, filed 5/25/79, now abandoned.

This invention is concerned with cephalosporin compounds possessing valuable antibiotic properties.

The cephalosporin compounds in this specification are named with reference to "cepham" after *J. Amer. Chem. Soc.*, 1962, 84, 3400, the term "cephem" referring to the basic cepham structure with one double bond.

Cephalosporin antibiotics are widely used in the treatment of diseases caused by pathogenic bacteria in human beings and animals, and are especially useful in the treatment of diseases caused by bacteria which are resistant to other antibiotics such as penicillin compounds, and in the treatment of penicillin-sensitive patients. In many instances it is desirable to employ a cephalosporin antibiotic which exhibits activity against both gram-positive and gram-negative microorganisms, and a significant amount of research has been directed to the development of various types of broad spectrum cephalosporin antibiotics.

Thus, for example, in our British Patent Specification No. 1,399,086, we describe a novel class of cephalosporin antibiotics containing a 7β-(α-etherified oximino)acylamido group, the oximino group having the syn configuration. This class of antibiotic compounds is characterised by high antibacterial activity against a range of gram-positive and gram-negative organisms coupled with particularly high stability to β-lactamases produced by various gram-negative organisms.

The discovery of this class of compounds has stimulated further research in the same area in attempts to find compounds which have improved properties, for example against particular classes of organisms especially gram-negative organisms.

In our British Patent Specification No. 1,496,757, we describe cephalosporin antibiotics containing a 7β-acylamido group of the formula

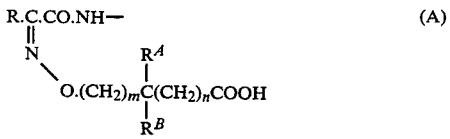

(A)

(wherein R is a thienyl or furyl group; $R^A$ and $R^B$ may vary widely and may, for example, be $C_{1-4}$ alkyl groups or together with the carbon atom to which they are attached form a $C_{3-7}$ cycloalkylidene group, and m and n are each 0 or 1 such that the sum of m and n is 0 or 1), the compounds being syn isomers or mixtures of syn and anti isomers containing at least 90% of the syn isomer. The 3-position of the cephalosporin molecule may be unsubstituted or may contain one of a wide variety of possible substituents. These compounds have been found to have particularly good activity against gram-negative organisms.

Other compounds of similar structure have been developed from these compounds in further attempts to find antibiotics having improved broad spectrum antibiotic activity and/or high activity against gram-negative organisms. Such developments have involved variations in not only the 7β-acylamido group in the above formula but also the introduction of particular groups in the 3-position of the cephalosporin molecule.

Thus, for example, in Belgian Patent Specification No. 852,427, there are described cephalosporin antibiotic compounds falling within the general scope of our British Patent Specification No. 1,399,086, and wherein the group R in formula (A) above may be replaced by a variety of different organic groups, including 2-aminothiazol-4-yl, and the oxygen atom in the oxyimino group is attached to an aliphatic hydrocarbon group which may itself be substituted by, for example, carboxy. In such compounds, the substituent at the 3-position may vary widely and may be inter alia an optionally substituted heterocyclic-thiomethyl group. Many examples of such groups are given in the specification including those in which the heterocyclic moiety of the group is a 3- to 8-membered heterocyclic ring containing 1 to 4 nitrogen atoms, e.g. an imidazolyl, pyrazolyl, pyridyl, pyrimidyl or tetrazolyl group which may be substituted, e.g. a 1-methyl-1H-tetrazol-5-yl group.

Furthermore, Belgian Patent Specification No. 836,813 describes cephalosporin compounds wherein the group R in formula (A) above may be replaced by, for example, 2-aminothiazol-4-yl, and the oxyimino group is a hydroxyimino or blocked hydroxyimino group, e.g. a methoxyimino group. In such compounds, the 3-position of the cephalosporin molecule is substituted by a methyl group which may itself be optionally substituted by any of a large number of residues of nucleophilic compounds therein described. Examples of such residues include the mercapto group which may be attached to a 5- or 6-membered heterocyclic ring, which may contain 1 to 4 heteroatoms selected from oxygen, sulphur and nitrogen, e.g. pyridyl, pyrimidyl, pyrazolyl, or imidazolyl, which rings may, if desired, be substituted for example by lower alkyl groups. In the above mentioned Specification no antibiotic activity is ascribed to such compounds which are only mentioned as intermediates for the preparation of antibiotics described in that specification.

Belgian Patent Specification No. 853,545 describes cephalosporin antibiotics wherein the 7β-acylamido side chain is primarily a 2-(2-aminothiazol-4-yl)-2-(syn)-methoxyimino-acetamido group and the substituent in the 3-position is broadly defined in a similar manner to that in the above-mentioned Belgian Patent Specification No. 836,813. Compounds specifically exemplified in the Specification include compounds in which the 3-position is substituted by various heterocyclic-thio methyl radicals including methyltetrazolylthiomethyl radicals.

We have now discovered that by an appropriate selection of a small number of particular groups at the 7β-position in combination with a heterocyclic-substituted thiomethyl group at the 3-position, cephalosporin compounds having particularly advantageous activity (described in more detail below) against a wide range of commonly encountered pathogenic organisms may be obtained.

The present invention provides cephalosporin antibiotics of the general formula

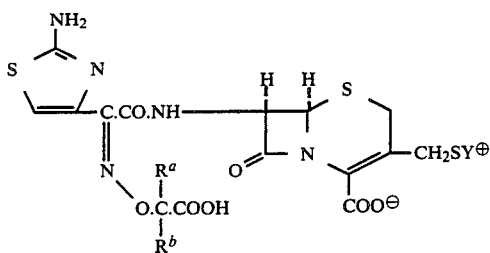

(wherein $R^a$ and $R^b$, which may be the same or different, each represent a $C_{1-4}$ alkyl group (preferably a straight chain alkyl group, i.e. a methyl, ethyl, n-propyl or n-butyl group and particularly a methyl or ethyl group) or $R^a$ and $R^b$ together with the carbon atom to which they are attached form a $C_{3-7}$ cycloalkylidene group, preferably a $C_{3-5}$ cycloalkylidene group; and $Y^\oplus$ represents a C-linked 5- or 6-membered heterocyclic ring containing at least one $C_{1-4}$ alkyl (e.g. methyl)-substituted quaternary nitrogen atom, which ring may also contain one or more sulphur atoms) and non-toxic salts and non-toxic metabolically labile esters thereof.

The compounds according to the invention are syn isomers. The syn isomeric form is defined by the configuration of the group

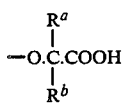

with respect to the carboxamido group. In this specification the syn configuration is denoted structurally as

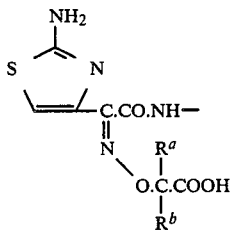

It will be understood that since the compounds according to the invention are geometric isomers, some admixture with the corresponding anti isomer may occur.

The invention also includes within its scope the solvates (especially the hydrates) of the compounds of formula (I). It also includes within its scope salts of esters of compounds of formula (I).

The compounds according to the present invention may exist in tautomeric forms (for example in respect of the 2-aminothiazolyl group) and it will be understood that such tautomeric forms, e.g. the 2-iminothiazolinyl form, are included within the scope of the invention. The compounds according to the present invention may also exist in various zwitterionic forms. In such zwitterionic forms, for example, either the carboxyl group in the 4-position or the carboxyl group in the 7-side chain may be deprotonated. These zwitterionic forms, and mixtures thereof, are included within the scope of the present invention.

It will also be appreciated that when $R^a$ and $R^b$ in the above formula represent different $C_{1-4}$ alkyl groups, the carbon atom to which they are attached will comprise a centre of asymmetry. Such compounds are diastereoisomeric and the present invention embraces individual diastereoisomers of these compounds as well as mixtures thereof.

In formula (I) above, the heterocyclic ring of the group $Y^\oplus$ may for example contain 1 to 4 nitrogen atoms and, if desired, one sulphur atom, particular examples of these heterocyclic rings including imidazolyl, pyrazolyl, pyridyl, pyrimidyl, pyrazinyl, pyridazinyl, triazolyl, tetrazolyl, thiazolyl, thiadiazolyl, and thiazolidinyl.

The compounds according to the invention exhibit broad spectrum antibiotic activity. Against gram-negative organisms the activity is unusually high. This high activity extends to many β-lactamase-producing gram-negative strains. The compounds also possess high stability to β-lactamases produced by a range of gram-negative organisms.

Compounds according to the invention have been found to exhibit unusually high activity against strains of Pseudomonas organisms, e.g. strains of *Pseudomonas aeruginosa* as well as high activity against various members of the Enterobacteriaceae (e.g. strains of *Escherichia coli, Klebsiella pneumoniae, Salmonella typhimurium, Shigella sonnei, Enterobacter cloacae, Serratia marcescens,* Providence species, *Proteus mirabilis* and especially indole-positive Proteus organisms such as *Proteus vulgaris* and *Proteus morganii*), and strains of *Haemophilus influenzae.*

The antibiotic properties of the compounds according to the invention compare very favourably with those of the aminoglycosides such as amikacin or gentamicin. In particular, this applies to their activity against strains of various Pseudomonas organisms which are not susceptible to the majority of existing commercially available antibiotic compounds. Unlike the aminoglycosides, cephalosporin antibiotics normally exhibit low toxicity in man. The use of aminoglycosides in human therapy tends to be limited or complicated by the high toxicity of these antibiotics. The cephalosporin antibiotics of the present invention thus possess potentially great advantages over the aminoglycosides.

Non-toxic salt derivatives which may be formed by reaction of either or both of the carboxyl groups present in the compounds of general formula (I) include inorganic base salts such as alkali metal salts (e.g. sodium and potassium salts) and alkaline earth metal salts (e.g. calcium salts); amino acid salts (e.g. lysine and arginine salts); organic base salts (e.g. procaine, phenylethylbenzylamine, dibenzylethylenediamine, ethanolamine, diethanolamine and N-methylglucosamine salts). Other non-toxic salt derivatives include acid addition salts, e.g. formed with hydrochloric, hydrobromic, sulphuric, nitric, phosphoric, formic and trifluoroacetic acids. The salts may also be in the form of resinates formed with, for example, a polystyrene resin or cross-linked polystyrene divinylbenzene copolymer resin containing amino or quarternary amino groups or sulphonic acid groups, or with a resin containing carboxyl groups, e.g. a polyacrylic acid resin. Soluble base salts (e.g. alkali metal salts such as the sodium salt) of compounds of formula (I) may be used in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

These and other salt derivatives such as the salts with toluene-p-sulphonic and methanesulphonic acids may be employed as intermediates in the preparation and/or purification of the present compounds of formula (I), for example in the processes described below.

Non-toxic metabolically labile ester derivatives which may be formed by esterification of either or both carboxyl groups in the parent compound of formula (I) include acyloxyalkyl esters, e.g. lower alkanoyloxy-methyl or -ethyl esters such as acetoxy-methyl or -ethyl or pivaloyloxy-methyl esters. In addition to the above ester derivatives, the present invention includes within its scope compounds of formula (I) in the form of other physiologically acceptable equivalents, i.e. physiologically acceptable compounds which, like the metabolically labile esters, are converted in vivo into the parent antibiotic compound of formula (I).

Examples of preferred compounds according to the present invention include those compounds of formula (I) wherein $Y^\oplus$ represents an aromatic heterocyclic ring containing 1 to 4 nitrogen heteroatoms (without any sulphur heteroatoms), particularly a ring containing 1 or 2 nitrogen heteroatoms, rings containing only one nitrogen heteroatom being especially preferred. Examples of such Y groups include 1-methylpyridinium, 1-methylpyrimidinium and 1,2-dimethylpyrazolium.

Thus a preferred group of compounds according to the invention by virtue of their high antibiotic activity are those of the general formula:

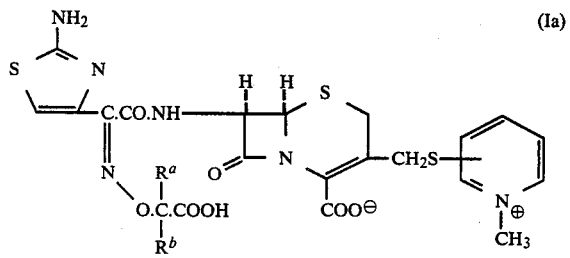

(wherein $R^a$ and $R^b$ have the above-defined meanings) and their non-toxic salts and non-toxic metabolically labile esters.

In formula (Ia) $R^a$ and $R^b$ preferably each represent a methyl group or together with the carbon atom to which they are attached form a cyclobutylidene group.

An outstanding compound of formula (Ia) is (6R,7R)-7-[(Z)-2-(2-aminothiazol-4-yl)-2-(1-carboxycyclobut-1-oxyimino)acetamido]-3-[(1-methylpyridinium-4-yl)-thiomethyl]ceph-3-em-4-carboxylate which has the formula

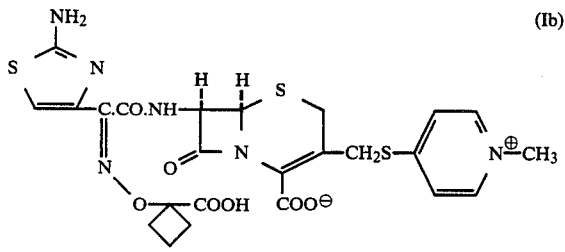

together with its non-toxic salts (e.g. sodium salt) and non-toxic metabolically labile esters. The compound of formula (Ib) possesses to an outstanding extent the general antibiotic properties set out above for the compounds of general formula (I). However one may emphasise its excellent activity against strains of Pseudomonas. The compound also possesses useful activity against strains of Staphylococcus aureas. The compound has excellent antibacterial properties which are not impaired by human serum, and, moreover, the effect of increased inocula against the compound is low. The compound is rapidly bactericidal at concentrations close to the minimum inhibitory concentration. It is well distributed in the bodies of small rodents giving useful therapeutic levels after subcutaneous injection. In primates the compound gives high and long lasting serum levels after intramuscular injection. The serum half-life in primates points to the probability of a comparatively long half-life in man, with the possibility of less frequent dosages being required for less serious infections. Experimental infections in mice with gram-negative bacteria were successfully treated using the compound and, in particular, excellent protection was obtained against strains of Pseudomonas aeruginosa, an organism normally not susceptible to treatment with cephalosporin antibiotics. The protection was comparable with the treatment with an aminoglycoside such as amikacin. Acute toxicity tests with the compound in mice gave $LD_{50}$ values in excess of 1.0 g/kg. No nephrotoxicity was observed in rats at dosages of 2.0 g/kg.

Another compound possessing not dissimilar properties to the compound of formula (Ib) is (6R,7R)-7-[(Z)-2-(2-aminothiazol-4-yl)-2-(2-carboxyprop-2-oxyimino)acetamido]-3-[(1-methylpyridinium-4-yl)-thiomethyl]ceph-3-em-4-carboxylate together with its non-toxic salts (e.g. the sodium salt) and non-toxic metabolically labile esters.

Other examples of preferred compounds according to the present invention include the following compounds of formula (I) and their non-toxic salts and non-toxic metabolically labile esters, namely:

(6R,7R)-7-[(Z)-2-(2-aminothiazol-4-yl)-2-(2-carboxy-prop-2-oxyimino)acetamido]-3-[(1-methylpyridinium-2-yl)-thiomethyl]ceph-3-em-4-carboxylate;

(6R,7R)-7-[(Z)-2-(2-aminothiazol-4-yl)-2-(1-carboxycyclobut-1-oxyimino)acetamido]-3-[(1-methylpyridinium-2-yl)-thiomethyl]ceph-3-em-4-carboxylate;

(6R,7R)-7-[(Z)-2-(2-aminothiazol-4-yl)-2-(2-carboxy-prop-2-oxyimino)acetamido]-3-[(1-methylpyridinium-3-yl)thiomethyl]ceph-3-em-4-carboxylate;

(6R,7R)-7-[(Z)-2-(2-aminothiazol-4-yl)-2-(2-carboxy-prop-2-oxyimino)acetamido]-3-[(1,2-dimethyl-pyrazolium-3-yl)thiomethyl]ceph-3-em-4-carboxylate;

(6R,7R)-7-[(Z)-2-(2-aminothiazol-4-yl)-2-(2-carbox-prop-2-oxyimino)acetamido]-3-[(1,3-dime-thylimidazolium-2-yl)thiomethyl]ceph-3-em-4-carboxylate; and (6R,7R)-7-[(Z)-2-(2-aminothiazol-4-yl)-2-(2-carboxy-prop-2-oxyimino)acetamido]-3-[(1-methylpyrimidinium-2-yl)thiomethyl]ceph-3-em-4-carboxylate.

Other compounds according to the present invention include for example those wherein the groups $R^a$, $R^b$ and Y in formula (I) are as follows:

| $R^a$ | $R^b$ | Y |
|---|---|---|
| (a) Alkyl groups | | |
| —CH$_3$ | —C$_2$H$_5$ | 1-methylpyridinium-2-yl |
| —C$_2$H$_5$ | " | " |

| -continued | | |
|---|---|---|
| —CH₃ | —C₂H₅ | 1-methylpyridinium-3-yl |
| —C₂H₅ | " | " |
| —CH₃ | —C₂H₅ | 1-methylpyridinium-4-yl |
| —C₂H₅ | " | " |
| —CH₃ | —C₂H₅ | 1-methyl-pyrimidinium-2-yl |
| —C₂H₅ | " | " |
| —CH₃ | —CH₃ | 1-methyl-pyrimidinium-4-yl |
| —CH₃ | —C₂H₅ | " |
| —C₂H₅ | " | " |
| —CH₃ | —C₂H₅ | 1,2-dimethyl-pyrazolium-3-yl |
| —C₂H₅ | " | " |
| —CH₃ | —C₂H₅ | 1,3-dimethyl-imidazolium-2-yl |
| —C₂H₅ | " | " |

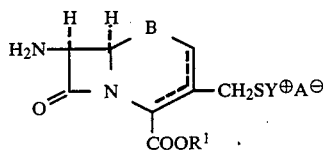

| | Y |
|---|---|
| (b) Cycloalkylidene groups | |
| cyclopropylidene | 1-methylpyridinium-2-yl |
| cyclopentylidene | " |
| cyclohexylidene | " |
| cyclopropylidene | 1-methylpyridinium-3-yl |
| cyclobutylidene | " |
| cyclopentylidene | " |
| cyclohexylidene | " |
| cyclopropylidene | 1-methylpyridinium-4-yl |
| cyclopentylidene | " |
| cyclohexylidene | " |
| cyclopropylidene | 1-methyl-pyrimidinium-2-yl |
| cyclobutylidene | " |
| cyclopentylidene | " |
| cyclopropylidene | 1,2-dimethyl-pyrazolium-3-yl |
| cyclobutylidene | " |
| cyclopentylidene | " |
| cyclopropylidene | 1,3-dimethyl-imidazolium-2-yl |
| cyclobutylidene | " |
| cyclopentylidene | " |

The compounds of formula (I) may be used for treating a variety of diseases caused by pathogenic bacteria in human beings and animals, such as respiratory tract infections and urinary tract infections.

According to another embodiment of the invention we provide a process for the preparation of an antibiotic compound of general formula (I) as hereinbefore defined or a non-toxic salt (including internal salt) or non-toxic metabolically labile ester thereof which comprises (A) acylating a compound of the formula

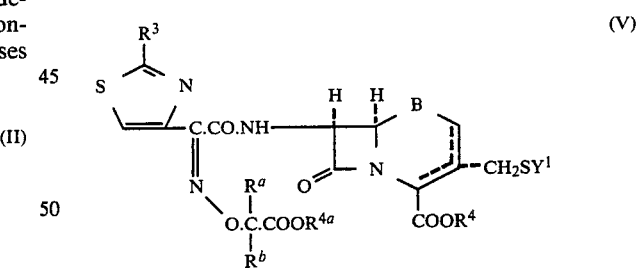

[wherein $Y^\oplus$ is as defined above; B is $>S$ or $>S \rightarrow O$ ($\alpha$- or $\beta$-); $R^1$ represents hydrogen or a carboxyl blocking group, e.g. the residue of an ester-forming aliphatic or araliphatic alcohol or an ester-forming phenol, silanol or stannanol (the said alcohol, phenol, silanol or stannanol preferably containing 1-20 carbon atoms); the dotted line bridging the 2-, 3-, and 4-positions indicates that the compound is a ceph-2-em or ceph-3-em compound and $A^\ominus$ is an anion such as a halide, e.g. chloride or bromide, or trifluoroacetate anion] or a salt, e.g. an acid addition salt (formed with, for example, a mineral acid such as hydrochloric, hydrobromic, sulphuric, nitric or phosphoric acid or an organic acid such as methanesulphonic or toluene-p-sulphonic acid) or an N-silyl derivative thereof, or alternatively a corresponding compound having a group of formula —COO$^\ominus$ at the 4-position, with an acid of formula (III)

(wherein $R^a$ and $R^b$ are as hereinbefore defined; $R^2$ represents a carboxyl blocking group, e.g. as described for $R^1$; and $R^3$ is an amino or protected amino group) or with an acylating agent corresponding thereto; (B) reacting a compound of formula (IV)

(wherein $R^a$, $R^b$, $R^3$, B and the dotted line are as defined above; $R^4$ and $R^{4a}$ may independently represent hydrogen or a carboxyl blocking group; and X is a replaceable residue of a nucleophile, e.g. an acetoxy or dichloroacetoxy group or a halogen atom such as chlorine, bromine or iodine) or a salt thereof with a sulphur nucleophile serving to form a group of formula —CH₂SY$^\oplus$ (wherein Y$^\oplus$ is as defined above) at the 3-position; or (C) reacting a compound of formula (V)

(wherein $R^a$, $R^b$, $R^3$, B and the dotted line are as defined above; $R^4$ and $R^{4a}$ in this instance are both carboxyl blocking groups; and $Y^1$ represents a C-linked 5- or 6-membered heterocyclic ring containing a tertiary nitrogen atom) with a C₁₋₄ alkylating agent serving to introduce a C₁₋₄ alkyl group as a substituent on the said tertiary nitrogen atom in the heterocyclic ring of the group $Y^1$; whereafter, if necessary and/or desired in each instance, any of the following reactions, in any appropriate sequence, are carried out:

(i) conversion of a Δ²-isomer into the desired Δ³-isomer, (ii) reduction of a compound wherein B is $>S \rightarrow O$ to form a compound wherein B is $>S$, (iii) conversion of a carboxyl group into a non-toxic salt or non-toxic metabolically labile ester function, and (iv) removal of any carboxyl blocking and/or N-protecting groups.

In the above-described process (A), the starting material of formula (II) is preferably a compound wherein B is >S and the dotted line represents a ceph-3-em compound.

Acylating agents which may be employed in the preparation of compounds of formula (I) include acid halides, particularly acid chlorides or bromides. Such acylating agents may be prepared by reacting an acid (III) or a salt thereof with a halogenating agent e.g. phosphorus pentachloride, thionyl chloride or oxalyl chloride.

Acylations employing acid halides may be effected in aqueous and non-aqueous reaction media, conveniently at temperatures of from −50° to +50° C., preferably −20° to +30° C., if desired in the presence of an acid binding agent. Suitable reaction media include aqueous ketones such as aqueous acetone, esters such as ethyl acetate, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula (III) may themselves be used as acylating agents in the preparation of compounds of formula (I). Acylations employing acids (III) are desirably conducted in the presence of a condensing agent, for example a carbodiimide such as N,N'-dicyclohexylcarbodiimide or N-ethyl-N'-γ-dimethylaminopropylcarbodiimide; a carbonyl compound such as carbonyldiimidazle; or an isoxazolium salt such as N-ethyl-5-phenylisoxazolium perchlorate.

Acylation may also be effected with other amide-forming derivatives of acids of formula (III) such as, for example, an activated ester, a symmetrical anhydride or a mixed anhydride (e.g. formed with pivalic acid or with a haloformate, such as a lower alkylhaloformate). Mixed anhydrides may also be formed with phosphorus acids (for example phosphoric or phosphorus acids), sulphuric acid or aliphatic or aromatic sulphonic acids (for example toluene-p-sulphonic acid). An activated ester may conveniently be formed in situ using, for example, 1-hydroxybenzotriazole in the presence of a condensing agent as set out above. Alternatively, the activated ester may be preformed.

Acylation reactions involving the free acids or their above-mentioned amide-forming derivatives are desirably effected in an anhydrous reaction medium, e.g. methylene chloride, tetrahydrofuran, dimethylformamide or acetonitrile.

If desired, the above acylation reactions may be carried out in the presence of a catalyst such as 4-dimethylaminopyridine.

The acids of formula (III) and acylating agents corresponding thereto may, if desired, be prepared and employed in the form of their acid addition salts. Thus, for example, acid chlorides may conveniently be employed as their hydrochloride salt, and acid bromides as their hydrobromide salts.

In process (B) above, the sulphur nucleophile may be used to displace a wide variety of substituents X from the cephalosporin of formula (IV). To some extent the facility of the displacement is related to the pKa of the acid HX from which the substituent is derived. Thus, atoms or groups X derived from strong acids tend, in general, to be more easily displaced than atoms or groups derived from weaker acids. The facility of the displacement is also related, to some extent, to the precise character of the sulphur nucleophile. The latter nucleophile may be employed for example in the form of an appropriate thiol or thione.

The displacement of X by the sulphur nucleophile may conveniently be effected by maintaining the reactants in solution or suspension. The reaction is advantageously effected using from 1 to 10 moles of the nucleophile.

Nucleophilic displacement reactions may conveniently be carried out on those compounds of formula (IV) wherein the substituent X is a halogen atom or an acyloxy group, for example as discussed below.

Acyloxy ggroups

Compounds of formula (IV) wherein X is an acetoxy group are convenient starting materials for use in the nucleophilic displacement reaction with the sulphur nucleophile. Alternative starting materials in this class include compounds of formula (IV) in which X is the residue of a substituted acetic acid e.g. chloroacetic acid, dichloroacetic acid and trifluoroacetic acid.

Displacement reactions on compounds (IV) possessing X substituents of this class, particularly in the case where X is an acetoxy group, may be facilitated by the presence in the reaction medium of iodide or thiocyanate ions.

The substituent X may also be derived from formic acid, a haloformic acid such as chloroformic acid, or a carbamic acid.

When using a compound of formula (IV) in which X represents an acetoxy or substituted acetoxy group, it is generally desirable that the group $R^4$ in formula (IV) should be a hydrogen atom and that B should represent >S. In this case, the reaction is advantageously effected in an aqueous medium.

Under aqueous conditions, the pH value of the reaction solution is advantageously maintained in the range 6–8, if necessary by the addition of a base. The base is conveniently an alkali metal or alkaline earth metal hydroxide or bicarbonate such as sodium hydroxide or sodium bicarbonate.

When using compounds of formula (IV) in which X is an acetoxy group, the reaction is conveniently effected at a temperature of 30° C. to 110° C., preferably 50° to 80° C.

Halogens

Compounds of formula (IV) in which X is a chlorine, bromine or iodine atom can also be conveniently used as starting materials in the nucleophilic displacement reaction with the sulphur nucleophilic. When using compounds of formula (IV) in this class, B may represent >S and $R^4$ may represent a carboxyl blocking group. The reaction is conveniently effected in a non-aqueous medium which preferably comprises one or more organic solvents, advantageously of a polar nature such as ethers, e.g. dioxan or tetrahydrofuran, esters, e.g. ethyl acetate, amides, e.g. formamide and N,N-dimethylformamide, and ketones e.g. acetone. Other suitable organic solvents are described in more detail in British Patent Specification No. 1,326,531. The reaction medium should be neither extremely acidic nor extremely basic.

In the case of reactions carried out on compounds of formula (IV) in which $R^4$ and $R^{4a}$ are carboxyl blocking groups and the resulting Y group contains a quaternary nitrogen atom, the product will be formed as the corresponding halide salt which may, if desired, be subjected to one or more ion exchange reactions to obtain a salt having the desired anion.

When using compounds of formula (IV) in which X is a halogen atom as described above, the reaction is conveniently effected at a temperature of $-20°$ to $+60°$, preferably $0°$ to $+30°$ C.

When the incoming nucleophile does not yield a compound containing a quaternized nitrogen atom, the reaction is generally effected in the presence of an acid scavenging agent for example a base such as triethylamine or calcium carbonate.

In process (C) above, the compound of formula (V) is advantageously reacted with an alkylating agent of the formula $R^5Z$ wherein $R^5$ is a $C_{1-4}$ alkyl group and Z is a leaving group such as a halogen atom (e.g. iodine, chlorine or bromine) or a hydrocarbylsulphonate (e.g. mesylate or tosylate) group. Alternatively, a di—$C_{1-4}$—alkyl sulphate, e.g. dimethyl sulphate, may be employed as the alkylating agent. Iodomethane is preferred as the alkylating agent. The alkylation reaction is preferably carried out at a temperature in the range of $0°$ to $60°$ C., advantageously $20°$ to $30°$ C. Where the alkylating agent is liquid under the reaction conditions, as in the case of iodomethane, this agent can itself serve as a solvent. Alternatively, the reaction may be conveniently effected in an inert solvent such as an ether e.g. tetrahydrofuran, an amide, e.g. dimethylformamide, a lower alkanol, e.g. ethanol, a lower dialkylketone, e.g. acetone, a halogenated hydrocarbon e.g. dichloromethane or an ester e.g. ethyl acetate.

The compound of formula (V) used as starting material in process (C) may be prepared for example by reaction of a compound of formula (IV) (as defined above) with an appropriate sulphur nucleophile in an analogous manner to the nucleophile displacement reaction described with respect to process (B). If desired the above nucleophile may be used in the form of a metal thiolate salt.

The reaction product may be separated from the reaction mixture, which may contain, for example, unchanged cephalosporin starting material and other substances, by a variety of processes including recrystallisation, ionophoresis, column chromatography and use of ion-exchangers (for example by chromatography on ion-exchange resins) or macroreticular resins.

$\Delta^2$-Cephalosporin ester derivatives obtained in accordance with the process of the invention may be converted into the corresponding $\Delta^3$-derivative by, for example, treatment of the $\Delta^2$-ester with a base, such as pyridine or triethylamine.

A ceph-2-em reaction product may also be oxidised to yield the corresponding ceph-3-em 1-oxide, for example by reaction with a peracid, e.g. peracetic or m-chloroperbenzoic acid; the resulting sulphoxide may, if desired, subsequently be reduced as described hereinafter to yield the corresponding ceph-3-em sulphide.

Where a compound is obtained in which B is $>S\rightarrow O$ this may be converted to the corresponding sulphide by, for example, reduction of the corresponding acyloxysulphonium or alkoxysulphonium salt prepared in situ by reaction with e.g. acetyl chloride in the case of an acetoxysulphonium salt, reduction being effected by, for example, sodium dithionite or by iodide ion as in a solution of potassium iodide in a water-miscible solvent e.g. acetic acid, acetone, tetrahydrofuran, dioxan, dimethylformamide or dimethylacetamide. The reaction may be effected at a temperature of from $-20°$ to $+50°$ C.

Metabolically labile ester derivatives of the compound of formula (I) may be prepared by reacting a compound of formula (I) or a salt or protected derivative thereof with the appropriate esterifying agent such as an acyloxyalkyl halide (e.g. iodide) conveniently in an inert organic solvent such as dimethylformamide or acetone, followed, where necessary, by removal of any protecting groups.

Base salts of the compound of formula (I) may be formed by reacting an acid of formula (I) with an appropriate base. Thus, for example, sodium or potassium salts may be prepared using the respective 2-ethylhexanoate or hydrogen carbonate salt. Acid addition salts may be prepared by reacting a compound of formula (I) or a metabolically labile ester derivative thereof with the appropriate acid.

Where a compound of formula (I) is obtained as a mixture of isomers, the syn isomer may be obtained by, for example, conventional methods such as crystallisation or chromatography.

For use as starting materials for the preparation of compounds of general formula (I) according to the invention, compounds of general formula (III) and acid halides and anhydrides corresponding thereto in their syn isomeric form or in the form of mixtures of the syn isomers and the corresponding anti isomers containing at least 90% of the syn isomer are preferably used.

Acids of formula (III) (provided that $R^a$ and $R^b$ together with the carbon atom to which they are attached do not form a cyclopropylidene group) may be prepared by etherification of a compound of formula

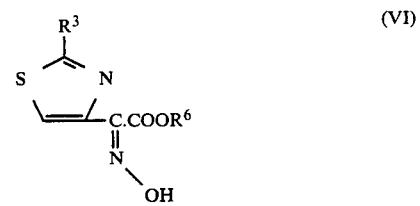

(wherein $R^3$ is as hereinbefore defined and $R^6$ represents a carboxyl blocking group), by reaction with a compound of general formula

(wherein $R^a$ and $R^b$ and $R^2$ are as hereinbefore defined and T is halogen such as chloro, bromo or iodo; sulphate, or sulphonate such as tosylate), followed by removal of the carboxyl blocking group $R^6$. Separation of isomers may be effected either before or after such etherification. The etherification reaction is generally carried out in the presence of a base, e.g. potassium carbonate or sodium hydride, and is preferably conducted in an organic solvent, for example dimethylsulphoxide, a cyclic ether such as tetrahydrofuran or dioxan, or an N,N-disubstituted amide such as dimethylformamide. Under these conditions the configuration of the oxyimino group is substantially unchanged by the etherification reaction. The reaction should be effected in the presence of a base if an acid addition salt of a compound of formula (VI) is used. The base should be used in sufficient quantity to neutralise rapidly the acid in question.

Acids of general formula (III) may also be prepared by reaction of a compound of formula

(VIII)

(wherein $R^3$ and $R^6$ are as hereinbefore defined) with a compound of formula

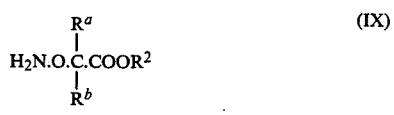

(IX)

(wherein $R^a$, $R^b$ and $R^2$ are as defined above), followed by removal of the carboxyl blocking group $R^6$, and where necessary by the separation of syn and anti isomers.

The last mentioned reaction is particularly applicable to the preparation of acids of formula (III) wherein $R^a$ and $R^b$ together with the carbon atom to which they are attached form a cyclopropylidene group. In this case, the relevant compounds of formula (IX) may be prepared in conventional manner, e.g. by means of the synthesis described in Belgian Patent Specification No. 866,422 for the preparation of t-butyl 1-amino-oxycyclopropane carboxylate.

The acids of formula (III) may be converted to the corresponding acid halides and anhydrides and acid addition salts by conventional methods, for example as described hereinabove.

Where X is a halogen (i.e. chlorine, bromine or iodine) atom in formula (IV), ceph-3-em starting compounds may be prepared in conventional manner, e.g. by halogenation of a 7β-protected amino-3-methylceph-3-em-4-carboxylic acid ester 1β-oxide, removal of the 7β-protecting group, acylation of the resulting 7β-amino compound to form the desired 7β-acylamido group, e.g. in an analogous manner to process (A) above, followed by reduction of the 1β-oxide group later in the sequence. This is described in British Pat. No. 1,326,531. The corresponding ceph-2-em compounds may be prepared by the method of Dutch published Patent Application No. 6,902,013 by reaction of a 3-methylceph-2-em compound with N-bromosuccinimide to yield the corresponding 3-bromomethylceph-2-em-compound.

Where X in formula (IV) is an acetoxy group, such starting materials may be prepared for example by acylation of 7-aminocephalosporanic acid, e.g. in an analogous manner to process (A) above. Compounds of formula (IV) in which X represents other acyloxy groups can be prepared by acylation of the corresponding 3-hydroxymethyl compounds which may be prepared for example by hydrolysis of the appropriate 3-acetoxymethyl compounds, e.g. as described for example in British Pat. Nos. 1,474,519 and 1,531,212.

Compounds of formula (II) may also be prepared in conventional manner, e.g. by nucleophilic displacement of a corresponding 3-acyloxymethyl or 3-halomethyl compound with the appropriate nucleophile, e.g. as described in British Pat. Nos. 1,012,943 and 1,241,657.

A further method for the preparation of the starting materials of formula (II) comprises deprotecting a corresponding protected 7β-amino compound in conventional manner, e.g. using $PCl_5$. A new compound of formula (II) is 7-amino-3-[(1-methylpyridinium-4-yl)thiomethyl]-ceph-3-em-4-carboxylate.

It should be appreciated that in some of the above transformations it may be necessary to protect any sensitive groups in the molecule of the compound in question to avoid undesirable side reactions. For example, during any of the reaction sequences referred to above it may be necessary to protect the $NH_2$ group of the aminothiazolyl moiety, for example by tritylation, acylation (e.g. chloroacetylation), protonation or other conventional method. The protecting group may thereafter be removed in any convenient way which does not cause breakdown of the desired compound, e.g. in the case of a trityl group by using an optionally halogenated carboxylic acid, e.g. acetic acid, formic acid, chloroacetic acid or trifluoroacetic acid or using a mineral acid, e.g. hydrochloric acid or mixtures of such acids, preferably in the presence of a protic solvent such as water, or, in the case of a chloroacetyl group, by treatment with thiourea.

Carboxyl blocking groups used in the preparation of compounds of formula (I) or in the preparation of necessary starting materials are desirably groups which may readily be split off at a suitable stage in the reaction sequence, conveniently at the last stage. It may, however, be convenient in some instances to employ non-toxic metabolically labile carboxyl blocking groups such as acyloxy-methyl or -ethyl groups (e.g. acetoxymethyl or-ethyl or pivaloyloxymethyl) and retain these in the final product to give an appropriate ester derivative of a compound of formula (I).

Suitable carboxyl blocking groups are well known in the art, a list of representative blocked carboxyl groups being included in British Pat. No. 1,399,086. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. Carboxyl blocking group(s) may subsequently be removed by any of the appropriate methods disclosed in the literature; thus, for example, acid or base catalysed hydrolysis is applicable in many cases, as are enzymically-catalysed hydrolyses.

The antibiotic compounds of the invention may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers, if necessary with an added preservative. The compositions may also take such forms as suspensions, solutions, or emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

If desired, such powder formulation may contain an appropriate non-toxic base in order to improve the water-solubility of the active ingredient and/or to ensure that when the powder is reconstituted with water, the pH of the resulting aqueous formulation is physiologically acceptable. Alternatively the base may be present in the water with which the powder is reconstituted. The base may be, for example, an inorganic base such as sodium carbonate, sodium bicarbonate or sodium acetate, or an organic base such as lysine or lysine acetate.

The antibiotic compounds may also be formulated as suppositories, e.g. containing conventional suppository bases such as cocoa butter or other glycerides.

Compositions for veterinary medicine may, for example, be formulated as in intramammary preparations in either long acting or quick-release bases.

The compositions may contain from 0.1% upwards, e.g. 0.1-99% of the active material, depending on the method of administration. When the compositions comprise dosage units, each unit will preferably contain 50-1500 mg of the active ingredient. The dosage as employed for adult human treatment will preferably range from 500 to 6000 mg per day, depending on the route and frequency of administration. For example, in adult human treatment 1000 to 3000 mg per day administered intravenously or intramuscularly will normally suffice. In treating Pseudomonas infections higher daily doses may be required.

The antibiotic compounds according to the invention may be administered in combination with other therapeutic agents such as antibiotics, for example penicillins or other cephalosporins.

The following Examples illustrate the invention. All temperatures are in °C. 'Petrol' means petroleum ether (b.p. 40°-60°).

Proton magnetic resonance (p.m.r.) spectra were determined at 100 MHz. The integrals are in agreement with the assignments, coupling constants, J, are in Hz, the signs not being determined; s=singlet, d=doublet, dd=double doublet, m=multiplet, q=quartet and Abq=AB quartet.

Preparation 1

Ethyl (Z)-2-(2-aminothiazol-4-yl)-2-(hydroxyimino)acetate

To a stirred and ice-cooled solution of ethyl acetoacetate (292 g) in glacial acetic acid (296 ml) was added a solution of sodium nitrite (180 g) in water (400 ml) at such a rate that the reaction temperature was maintained below 10° C. Stirring and cooling were continued for about 30 min., when a solution of potassium chloride (160 g) in water (800 ml) was added. The resulting mixture was stirred for one hour. The lower oily phase was separated and the aqueous phase was extracted with diethyl ether. The extract was combined with the oil, washed successively with water and saturated brine, dried, and evaporated. The residual oil, which solidified on standing, was washed with petrol and dried in vacuo over potassium hydroxide, giving ethyl (Z)-2-(hydroxyimino)-3-oxobutyrate (309 g).

A stirred and ice-cooled solution of ethyl (Z)-2-(hydroxyimino)-3-oxobutyrate (150 g) in dichloromethane (400 ml) was treated dropwise with sulphuryl chloride (140 g). The resulting solution was kept at room temperature for 3 days, then evaporated. The residue was dissolved in diethyl ether, washed with water until the washings were almost neutral, dried, and evaporated. The residual oil (177 g) was dissolved in ethanol (500 ml) and dimethylaniline (77 ml) and thiourea (42 g) were added with stirring. After two hours, the product was collected by filtration, washed with ethanol and dried to give the title compound (73 g); m.p. 188° C. (decomp.).

Preparation 2

Ethyl (Z)-2-hydroxyimino-2-(2-tritylaminothiazol-4-yl)acetate, hydrochloride

Trityl chloride (16.75 g) was added portionwise over 2 hours to a stirred and cooled (−30°) solution of the product of Preparation 1 (12.91 g) in dimethylformamide (28 ml) containing triethylamine (8.4 ml). The mixture was allowed to warm to 15° over one hour, stirred for a further 2 hours and then partitioned between water (500 ml) and ethyl acetate (500 ml). The organic phase was separated, washed with water (2×500 ml) and then shaken with 1N HCl (500 ml). The precipitate was collected, washed successively with water (100 ml), ethyl acetate (200 ml) and ether (200 ml) and dried in vacuo to provide the title compound as a white solid (16.4 g); m.p. 184° to 186° (decomp).

Preparation 3

Ethyl (Z)-2-(2-t-butoxycarbonylprop-2-oxyimino)-2-(2-tritylaminothiazol-4-yl)acetate Potassium carbonate (34.6 g) and t-butyl 2-bromo-2-methylpropionate (24.5 g) in dimethylsulphoxide (25 ml) were added to a stirred solution under nitrogen of the product of Preparation 2 (49.4 g) in dimethylsulphoxide (200 ml) and the mixture was stirred at room temperature for 6 hours. The mixture was poured into water (2 l), stirred for 10 mins., and filtered. The solid was washed with water and dissolved in ethyl acetate (600 ml). The solution was washed successively with water, 2N hydrochloric acid, water, and saturated brine, dried, and evaporated. The residue was recrystallised from petroleum ether (b.p. 60°-80°) to give the title compound (34 g), m.p. 123.5° to 125°.

Preparation 4

(Z)-2-(2-t-Butoxycarbonylprop-2-oxyimino)-2-(2-tritylaminothiazol-4-yl)acetic acid The product of Preparation 3 (2 g) was dissolved in methanol (20 ml) and 2N sodium hydroxide (3.3 ml) was added. The mixture was refluxed for 1.5 hours and then concentrated. The residue was taken up in a mixture of water (50 ml), 2N hydrochloric acid (7 ml), and ethyl acetate (50 ml). The organic phase was separated, and the aqueous phase extracted with ethyl acetate. The organic solutions were combined, washed successively with water and saturated brine, dried, and evaporated. The residue was recrystallised from a mixture of carbon tetrachloride and petrol to give the title compound (1 g), m.p. 152° to 156° (decomp).

Preparation 5

Ethyl (Z)-2-(2-tritylaminothiazol-4-yl)-2-(1-t-butoxycarbonyl-cyclobut-1-oxyimino)acetate The product of Preparation 2 (55.8 g) was stirred under nitrogen in dimethylsulphoxide (400 ml) with potassium carbonate (finely ground, 31.2 g) at room temperature. After 30 minutes, t-butyl 1-bromocyclobutane carboxylate (29.2 g) was added. After 8 hours further potassium carbonate (31.2 g) was added. More potassium carbonate (6×16 g portions) was added during the next three days and further t-butyl 1-bromocyclobutane carboxylate (3.45 g) was added after 3 days. After 4 days in all, the mixture was poured into icewater (ca. 3 liters) and the solid was collected by filtration and washed well with water and petrol. The solid was dissolved in ethyl acetate and the solution washed with brine (twice), dried with magnesium sulphate and evaporated to a foam. This foam was dissolved in ethyl acetate-petrol (1:2) and filtered through silica gel (500 g). Evaporation gave the title compound (60 g) as a foam, $v_{max}$ (CHBr$_3$) 3400 (NH) and 1730 cm$^{-1}$ (ester).

Preparation 6

(Z)-2-(1-t-Butoxycarbonylcyclobut-1-oxyimino)-2-(2-tritylaminothiazol-4-yl)acetic acid A mixture of the product of Preparation 5 (3.2 g) and potassium carbonate (1.65 g) was refluxed in methanol (180 ml) and water (20 ml) for 9 hours and the mixture was cooled to room temperature. The mixture was concentrated and the residue partitioned between ethyl acetate and water, to which was added 2N HCl (12.2 ml). The organic phase was separated and the aqueous phase extracted with ethyl acetate. The combined organic extracts were washed with saturated brine, dried and evaporated to give the title compound (2.3 g); $\lambda_{max}$ (ethanol) 265 nm (E$_{1\ cm}$1% 243).

Preparation 7

Diphenylmethyl (1S,6R,7R)-3-Bromomethyl-7-[(Z)-2-(2-t-butoxycarbonylprop-2-oxyimino)-2-(2-tritylaminothiazol-4-yl)acetamido]ceph-3-em-4-carboxylate, 1-Oxide Diphenylmethyl (1S,6R,7R)-7-amino-3-bromomethylceph-3-em-4-carboxylate, 1-oxide hydrobromide (1.40 g) was shaken with dichloromethane (100 ml) and half-saturated aqueous sodium bicarbonate solution (100 ml). The filtered organic layer was dried over anhydrous sodium sulphate and evaporated to give the free 7-amine as a white solid (1.05 g). The solid (1.015 g) and the product of Preparation 4 (1.23 g) were dissolved in N,N-dimethylformamide (21 ml) and to the solution was added 1-hyroxybenzotriazole monohydrate (394 mg) and N,N'-dicyclohexylcarbodiimide (530 mg). The solution, which soon developed a precipitate, was stirred at 20° for 18 hours, and was then filtered, and the residue was washed with ethyl acetate (2×50 ml). The combined fitrate and washings were washed with 2N-hydrochloric acid (2×100 ml) and water (2×100 ml). The organic layer was dried over anhydrous sodium sulphate and evaporated to a brown foam (2.645 g) which was triturated with ether:petrol—1:1 (50 ml) to give a solid (2.3 g). The solid was partly purified on a column of silica gel (70 to 230 mesh, 50 g) eluted with chloroform in 75 ml fractions. Fractions 3 and 4 yielded a foam (1.085 g) which was purified by preparative thin-layer chromatography in ethyl acetate:-toluene=1:3 to give a product (R$_f$ca. 0.5) as a foam (494 mg). A solution of the product in a little ethyl acetate was added to stirred petrol and the precipitate was filtered off and dried in vacuo to give the title compound (424 mg) as a solid, $[\alpha]_D+6°$ (CHCl$_3$, c 0.53); $\lambda_{max}$ (ethanol) 267.5 nm (E$_{1\ cm}$1% 188), $\lambda_{inf}$ 237.5 nm (E$_{1\ cm}$1% 249), $\lambda_{inf}$ 260 nm (E$_{1\ cm}$1% 191), $\lambda_{inf}$ 273 nm (E$_{1\ cm}$1% 184).

EXAMPLE 1

(a) t-Butyl (6R,7R)-3-Acetoxymethyl-7-[(Z)-2-2-t-butoxycarbonyl-prop-2-oxyimino)-2-(2-tritylaminothiazol-4-yl)acetamido]ceph-3-em-4-carboxylate A stirred solution of the product of Preparation 4 (572 mg) and t-butyl (6R,7R)-3-acetoxymethyl-7-aminoceph-3-em-4-carboxylate (328 mg) in dimethylformamide (10 ml) was cooled to 0°, and 1-hydroxybenzotriazole (150 mg) was added, followed by dicyclohexylcarbodiimide (225 mg). The mixture was warmed to room temperature, stirred for 5 hours, and allowed to stand overnight. The mixture was filtered, and the white solid washed with a little ether. The filtrate and washings were diluted with water (50 ml) and extracted with ethyl acetate. The organic extracts were combined, washed successively with water, 2N hydrochloric acid, water, sodium bicarbonate solution, and saturated brine, dried and evaporated. The residue was eluted through a silica column with ether. The product-containing eluate was collected and concentrated to give the title compound (533 mg). A portion was recrystallised from di-isopropyl ether and had m.p. 103° to 113° (decomp.); $[\alpha]_D^{20}+8.5°$ (c 1.0, DMSO).

(b) (6R,7R)-3-Acetoxymethyl-y-[(Z)-2-(2-aminothiazol-4-yl)-2-(2-carboxyprop-2-oxyimino)acetamido]ceph-3-em-4-carboxylic acid Trifluoroacetic acid (18 ml) was added to a solution of the product of Stage (a) (2.4 g) in anisole (18 ml) at 0°. The mixture was stirred at room temperature for 2 hours and concentrated. The residue was dissolved in ethyl acetate and extracted with saturated sodium bicarbonate solution. The pH of the aqueous extracts was adjusted to 6, and the solution washed with ethyl acetate. The aqueous phase was acidified to pH 1.5 under ethyl acetate, saturated with sodium chloride, and extracted with ethyl acetate. The combined organic extracts were washed with saturated brine, dried, and evaporated. The residue was dissolved in warm 50% formic acid (20 ml) and allowed to stand for 2 hours. The mixture was diluted with water (50 ml), and filtered. The filtrate was concentrated. The residue was taken up in water (50 ml), refiltered, and lyophilized to give the title compound (920 mg), $\lambda_{max}$ (pH 6 buffer) 236 nm (E$_{1\ cm}$1% 250), $\lambda_{inf}$ 255 nm (E$_{1\ cm}$1% 235), 296 nm (E$_{1\ cm}$1% 103); $[\alpha]_D^{20}+20.0°$ (c 1.0, DMSO).

(c)
(6R,7R)-7-[(Z)-2-(2-Aminothiazol-4-yl)-2-(2-carboxy-prop-2-oxyimino)acetamido]-3-(1-methylpyridinium-2-ylthiomethyl)ceph-3-em-4-carboxylate, mono-sodium salt The product of stage (b) (1.58 g) and sodium hydrogen carbonate (0.50 g.) were warmed with water (2 ml), and the mixture was then treated successively with N-methylpyrid-2-thione (564 mg.), sodium iodide (2.7 g) and sodium bicarbonate (ca. 400 mg., to give a mixture of pH 7). Water (0.4 ml) was added and the mixture was heated under nitrogen at 65° for 5 hours. The cooled mixture was then applied to a column of Amberlite XAD-2 resin (100 g.) and eluted with water in 100 ml. fractions (fractions 1 to 10) and then water:ethanol 3:1 in 100 ml, fractions (11 to 14). Fractions 10 to 12 were combined and evaporated to 250 ml. and washed with ether (4×125 ml.) and lyophilised to a pale brown residue (594 mg.) The residue (500 mg.) was dissolved in water (150 ml.) and the solution was washed with ethyl acetate (3×15 ml.) and lyophilised in the presence of formic acid to a foam which was triturated with ether and dried in vacuo to give the title compound as a formate salt (464 mg), $\lambda_{max}$ (pH 6 buffer) 241 nm ($E_{1\ cm}^{1\%}$ 288), $\lambda_{inf}$ 261 nm ($E_{1\ cm}^{1\%}$ 261), $\lambda_{inf}$ 304 nm ($E_{1\ cm}^{1\%}$ 174); $\nu_{max}$ (Nujol) 1538, 1670 (CONH), 1600 (broad; $CO_2^-$), 1767 cm$^{-1}$ ($\beta$-lactam).

EXAMPLE 2

(a) t-Butyl (6R,7R)-3-Acetoxymethyl-7-[(Z)-2-(1-t-butoxycarbonylcyclobut-1-oxyimino)-2-(2-tritylaminothiazol-4-yl)acetamido]ceph-3-em-4-carboxylate A stirred solution of the product of Preparation 6 (24.2 g) and t-butyl (6R,7R)-3-acetoxymethyl-7-aminocheph-3-em-carboxylate (13.6 g) in dimethylformamide (300 ml) was cooled to 0°, treated with 1-hydroxybenzotriazole monohydrate (4.5 g), followed by dicyclohexylcarbodiimide (6.4 g) and the product isolated substantially as described in Example 1 (a) to give the title compound (12.8 g), m.p. 113.5° to 116.5° (decomp), $[\alpha]_D^{20}+15.0°$ (c 1.0, DMSO).

(b) (6R,7R)-3-Acetoxymethyl-7-[(Z)-2-(2-aminothiazol-4-yl)-2-(1-carboxycyclobut-1-oxyimino)acetamido]ceph-3-em-4-carboxylic acid Trifluoroacetic acid (100 ml) was added to a mixture of the product of Stage (a) (12.5 g) and anisole (5 ml) at 0°. The mixture was treated substantially as described in Example 1 (b) to give the title compound (4 g), $\lambda_{max}$ (pH 6 buffer) 246 nm ($E_{1\ cm}^{1\%}$ 264), $\lambda_{inf}$ 295 nm ($E_{1\ cm}^{1\%}$ 118), $[\alpha]_D^{20}+27.3°$ (c 1.0, DMSO).

(c) (6R,7R)-7-[(Z)-2-(2-Aminothiazol-4-yl)-2-(1-carboxycyclobut-1-oxyimino)acetamido]-3-(1-methylpyridinium-2-ylthiomethyl)ceph-3-em-4-carboxylate, mono-sodium salt The product from Stage (a) (1.60 g) and sodium bicarbonate (0.50 g) were warmed with water (2 ml) and to the suspension was added 1-methylpyrid-2-thione (564 mg) and then more sodium bicarbonate (ca 350 mg) to give a mixture of pH ca 6.5. Sodium iodide (2.7 g) was added and the slightly cloudy solution was heated at 65° for 5 hours and then cooled and applied to a column of Amberlite XAD-2 (100 g). The column was eluted with water in ca 150 ml. fractions (1 to 5) and then with water:ethanol=3:1 in 150 ml. fractions (6 to 10). Fractions 4 to 7 were combined and the ethanol was removed by evaporation. The solution was washed with ethyl acetate (3×300 ml) and ether (200 ml) and evaporated until the organic solvents had been removed. It was then lyophilised to give a brown foam which was washed with ether and filtered and dried in vacuo to give the title compound (816 mg) as a foam, $[\alpha]_D+21°$ ($H_2O$:EtOH 1:1, c 0.84); $\lambda_{max}$ (pH 6 buffer) 248 nm ($E_{1\ cm}^{1\%}$ 294), $\lambda_{max}$ 305.5 nm ($E_{1\ cm}^{1\%}$ 191).

EXAMPLE 3

(a) (6R,7R)-3-Acetoxymethyl-7[(Z)-2-(2-aminothiazol-4-yl)-2-(2-carboxyprop-2-oxyimino)acetamido]ceph-3-em-4-carboxylic acid, Trifluoroacetate salt The product from Example 1 (a) (31 g) was dissolved in trifluoroacetic acid (90 ml) with ice-water cooling. After five minutes the mixture was warmed to 20°. After one hour the solution was poured into water (900 ml). Five minutes later, ether (450 ml) was added and the mixture was stirred for ten minutes. The ether layer, after separation, was extracted with further water (5 ml). The combined aqueous layers were washed with ether three times, on each occasion the organic layer being back extracted with water. The combined aqueous layers were evaporated to dryness and the residue was triturated with ether and dried to give the title compound (15.4 g) $\nu_{max}$ (Nujol) 3700–2200 (OH and $N^{\oplus}H_3$), 1784 ($\beta$-lactam), 1730 (ester), 1670 and 1545 (amide), 1680 (acids) and 1650 cm$^{-1}$ ($CF_3COO^{\ominus}$).

(b) (6R,7R)-7-[(Z)-2-(2-Aminothiazol-4-yl)-2-(2-carboxyprop-2-oxyimino)acetamido]-3-[(1-methylpyridinium-4-yl)thiomethyl]ceph-3-em-4-carboxylate mono-sodium salt A suspension of the product from Stage (a) (2.11 g) in water (3 ml) was treated portionwise with sodium bicarbonate (1.06 g) and warmed until effervescence ceased. The solution was treated successively under nitrogen with sodium iodide (4 g) and N-methylpyrid-4-thione (0.75 g), and kept at 70° for 4 hours.

The mixture was cooled and diluted with water and the resulting solution was poured into acetone (800 ml) with vigorous stirring. The precipitated material was isolated by filtration and washed with a little acetone and some ether and dried in vacuo to give a powder (2.97 g).

The product was purified by dissolving it in water (10 ml) and applying the solution to a column (ca. 330 mm×25 mm) containing "Amberlite" XAD-2 resin (100 g). The column was eluted with water (9×50 ml fractions collected) followed by 25% ethanol in water (7×50 ml fractions collected). Appropriate fractions were combined; ethanol removed in vacuo and the residue freeze-dried to give the title compound in two crops:

(i) 0.253 g (isolated from the aqueous fractions) had $\lambda_{max}$ (pH 6 buffer) 231.5 nm ($E_{1\ cm}^{1\%}$369) and 303 nm ($E_{1\ cm}^{1\%}$336) with an inflection at 255 nm ($E_{1\ cm}^{1\%}$268) and (ii) 0.900 g (isolated from the aqueous ethanol fractions) had $\lambda_{max}$ (pH 6 buffer) 231.5 nm ($E_{1\ cm}^{1\%}$378) and 303 nm ($E_{1\ cm}^{1\%}$379) with an inflection at 255 nm ($E_{1\ cm}^{1\%}$275) and $\tau$($D_2O$) 1.68 (d, J 6 Hz) and 2.23 (d, J 6

Hz) (pyridyl protons), 3.5 (s, thiazol-5-yl proton), 4,30 (d, J 5 Hz, 7—H), 4.84 (d, J 5 Hz, 6—H), 5.72 (obscured ABq, 3—CH$_2$), 5.88 (s, N+CH$_3$), 6.44 (centre of ABq, J 15 Hz, 2—H$_2$) and 8.55 (s, CMe$_2$).

EXAMPLE 4

(a) t-Butyl (6R,7R)-3-Acetoxymethyl-7-[(Z)-2-(1-t-butoxycarbonylcyclobut-1-oxyimino)-2-(2-tritylaminothiazol-4-yl)acetamido]ceph-3-em-4-carboxylate A stirred solution of the product of Preparation 6 (24.2 g) and t-butyl (6R, 7R)-3-acetoxymethyl-7-aminoceph-3-em-4-carboxylate (13.6 g) in dimethylformamide (300 ml) was cooled to 0°, and 1-hydroxybenzotriazole monohydrate (4.5 g) added, followed by dicyclohexylcarbodiimide (6.4 g). The mixture was warmed to room temperature and stirred overnight. The mixture was filtered, and the white solid washed with a little ether. The filtrate and washings were diluted with water (1.5l) and extracted with ethyl acetate. The organic extracts were combined, washed successively with water and saturated brine, dried, and evaporated. The residue was taken up in ether, filtered, and re-evaporated. The required product was isolated after elution through two silica columns with ether and concentrating the appropriate fractions. The residues were recrystallised from di-isopropyl ether to give the title compound (12.8 g), m.p. 113.5° to 116.5°; $[\alpha]_D^{20}$ + 15.0° (c, 1.0, DMSO).

(b) (6R,7R)-3-Acetoxymethyl-7-[(Z)-2-(2-Aminothiazol-4-yl)-2-(1-carboxycyclobut-1-oxyimino)acetamido]ceph-3-em-4-t-butoxycarboxylic Acid Hydrochloride t-Butyl(6R,7R)-3-acetoxymethyl-7-[(Z)-2-(1-t-butoxycarbonylcyclobut-1-oxyimino)-2-(2-tritylaminothiazol-4-yl)acetamido]ceph-3-em-4-carboxylate (17.9 g) in formic acid (72 ml) was cooled to +12° and concentrated hydrochloric acid (6 ml) added. The mixture was stirred for 1½ hours at 18°–20° and then cooled to 6°. The solid was filtered off, washed with formic acid and the combined filtrate and was added over 15 minutes to stirred isopropyl ether (2 l). The solid was filtered off, washed with isopropyl ether (25 ml) and dried at 40° in vacuo to give the title compound (11.47 g), $\tau$(DMSO d$_6$) 0.29 (d, J 9), 2.98 (s, thiazol-5-yl proton), 4.10 (dd, J4 and 9, 7—H), 4.78 (d, J 4, 6—H), 4.98 and 5.29 (ABq, J 13, 3—CH$_2$—), 6.38 (s, 2—H$_2$) 7.2–7.8 and 7.8–8.3 (cyclobutyl protons), 7.98 (s, OCOCH$_3$).

(c) (6R,7R)-7-[(Z)-2-(2-Aminothiazol-4-yl)-2-(1-carboxycyclobut-1-oxyimino)acetamido]-3-(1-methylpyridinium-4-ylthiomethyl)ceph-3-em-4-carboxylate A suspension of (6R,7R)-3-acetoxymethyl-7-[(Z)-2-(2-aminothiazol-4-yl)-2-(1-carboxycyclobut-1-oxyimino)acetamido]ceph-3-em-4-carboxylic acid hydrochloride (2.30 g) in water (5 ml) was treated portionwise with sodium bicarbonate (1.06 g) and warmed until effervescence ceased. Sodium iodide (4 g) was added to the solution followed by N-methylpyrid-4-thione (0.75 g). The mixture was covered with nitrogen and incubated at 70° for 4 hours.

The resulting solution was cooled to room temperature and poured into stirred acetone (800 ml). The precipitated solid was isolated by filtration, washed with acetone (10 ml), diethyl ether (10 ml), and dried in vacuo to give a powder (2.7 g).

The product was dissolved in water (10 ml) and the pH of the solution adjusted to 4.5 with acetic acid. The solution was treated with a mixture of "Amberlite" LA2 resin (10 ml), ether acetate (10 ml) and acetic acid (0.75 ml) and stirred at ambient temperature for 1 hour. The aqueous layer was separated and washed with ethyl acetate (5 ml). Ethyl acetate dissolved in the aqueous extract was removed by rotary evaporation. The resulting solution was readjusted to pH 4.5 with acetic acid.

The solution was run onto a column (ca. 330 mm × 25 mm) of "Amberlite" XAD-2 resin. The column was eluted with water (ca. 1.2 l), followed by water/ethanol (2/1). Appropriate fractions (ca. 1.2 l) were combined and reduced to a small volume (ca. 25 ml) by rotary evaporation. The residue was freeze-dried to give the title compound (530 mg.).

This material had $\lambda_{max}$ (pH 6 buffer), 231 nm (E$_1$ $_{cm}$$^{1\%}$351) and 303 nm (E$_1$ $_{cm}$$^{1\%}$428) with an inflection at 255 nm (E$_1$ $_{cm}$$^{1\%}$267). $\tau$(D$_2$O+NaHCO$_3$) 1.64 (d, J 6 Hz) and 2.21 (d, J 6 Hz) (pyridyl protons), 3.07 (s, thiazol-5-yl proton), 4.21 (d, J 4 Hz, 7—H), 4.75 (d, J 4 Hz, 6—H), 5.5 to 5.8 (obscured ABq, 3—CH$_2$), 5.84 (s, N+CH$_3$), 6.4 (centre of ABq J 15 Hz, 2—H$_2$), 7.58 and 8.1 (cyclobutyl protons).

EXAMPLE 5

(a) Diphenylmethyl (6R,7R)-7-[(Z)-2-(2-t-butoxycarbonylprop-2-oxyimino)-2-(2-tritylaminothiazol-4-yl)-acetamido]-3-bromomethylceph-3-em-4-carboxylate Phosphorus pentachloride (8.8 g) was dissolved with stirring in methylene chloride (400 ml). The solution was cooled to −20° C. and treated with the product of Preparation 4 (22.8 g) and the resultant clear solution stirred for ca 30 min at −15° C. Triethylamine (15.8 ml) was added and the mixture maintained at −15° C. for a further 5 min. before being added over 5 min. to a solution of diphenylmethyl (6R,7R)-7-amino-3-bromomethylceph-3-em-4-carboxylate hydrochloride (19.8 g) and triethylamine (5.6 ml) in methylene chloride (400 ml) stirred and maintained throughout at −15° to −20° C. The cooling was removed after 10 min and the mixture was stirred whilst the temperature rose to ambient over ca 30 min.

The mixture was poured into water (1 l) and methylene chloride (400 ml), shaken and the organic layer collected. The water was backwashed with methylene chloride (100 ml). The initial methylene chloride layer was washed with dilute sodium bicarbonate solution (to ca pH 8) and then this aqueous layer further washed with the backwash. The organic layers were combined and washed with half saturated brine solution. After drying the methylene chloride layer over magnesium sulphate the solvent was evaporated to afford a dry foam-solid. This was collected from the evaporation flask and dried in vacuo at 40° to afford the title compound (40.25 g) as a buff solid $\tau$(CDCl$_3$) 3.03 (s, —CH.Ph$_2$), 3.27 (s, thiazol-5-yl proton), 4.04 (dd, J 4 Hz+9 Hz, 7—H), 5.0 (d, J 4 Hz, 6—H), 5.72 (s, 3—CH$_2$, 6.3–6.7 (ABq 2—H$_2$), 8.37+8.41 (2×s, C—Me$_2$).

(b) Diphenylmethyl (6R,7R)-7-[(Z)-2-(2-t-butoxycarbonylprop-2-oxyimino)-2-(2-tritylaminothiazol-4-yl)-acetamido]-3-(1-methylpyridinium-4-ylthiomethyl)ceph-3-em-4-carboxylate bromide The product from Stage (a) (40 g), was dissolved in tetrahydrofuran (500 ml) and whilst being stirred was treated with N-methylpyrid-4-thione (5.0 g). After stirring at ambient temperature for 6 hours diethyl ether (2.0 l) was added. The mixture was stirred for 1 hour then cooled at 0° for 16 hours. The solid was removed by filtration, washed well with diethyl ether and dried for 16 hours in vacuo to give the title compound, (39.9 g); $\tau$(CDCl$_3$) 1.1–1.3 (broad s, pyridinium protons adjacent to N—Me), 2.2–2.4 (broad d, pyridinium protons adjacent to C—S), 3.07 (s, C$\underline{H}$.Ph$_2$), 3.27 (s, thiazol-5-yl proton), 3.36 (broad s Ph$_3$CN$\underline{H}$), 3.9–4.2 (dd, J 5 Hz+9 Hz 7—$\underline{H}$), 4.90 (d, J 5 Hz, 6—H), 5.64 (broad s C3—C$\underline{H}_2$+N$^+$Me) 6.1–6.6 (broad m, 2—H$_2$), 8.38+8.40 (2×s, C—Me$_2$): $\nu_{max}$ (Nujol) 1802 ($\beta$-lactam), 1708 cm$^{-1}$ (CO$_2$H).

(c) (6R,7R)-7-[(Z)-2-(2-Aminothiazol-4-yl)-2-(2-carboxyprop-2-oxyimino)acetamido]-3-(1-methylpyridinium-4-ylthiomethyl)ceph-3-em-4-carboxylate The product from Stage (b) (40 g) was taken up in trifluoroacetic acid (320 ml) and anisole (80 ml) and stirred in an ice bath for 1½ hours. The solution was poured into water (3 l) and diethyl ether (1.5 l) and shaken vigorously. The aqueous layer was separated and washed further with diethyl ether (3×1.5 l) before being evaporated to dryness at ca 50° C. in vacuo. The resultant foam was triturated with acetone ca 500 ml and the solid filtered, washed with diethyl ether and dried in vacuo at 40° to give the title compound (12.25 g) whose nmr spectroscopic properties resembled those of the product of Example 3 (b). $\lambda_{max}$ (pH 6 buffer) 230.5 nm (E$_{1\ cm}^{1\%}$320), 303 nm (E$_{1\ cm}^{1\%}$385) and $\lambda_{inf}$ 258 nm (E$_{1\ cm}^{1\%}$233). Fluorine assay (2.8%) indicated that the product contained some trifluoracetic acid.

EXAMPLE 6

(a) Diphenylmethyl (6R,7R)-7-amino-3-(1-methylpyridinium-4-ylthiomethyl)-ceph-3-em-4-carboxylate bromide Diphenylmethyl (6R,7R)-7-amino-3-bromomethylceph-3-em-4-carboxylate hydrochloride (500 mg) was suspended in tetrahydrofuran (20 ml) and treated with triethylamine (0.14 ml). After stirring for ca 5 minutes at ca 0° the solution was clarified and treated with N-methylpyrid-4-thione (150 mg). The mixture was stirred for 2 hours at ambient temperature, then stored at 0° for 16 hours. The white solid was filtered off, washed with tetrahydrofuran and diethyl ether and dried in vacuo at ambient temperature for 16 hours to yield the title compound (500 mg) $\tau$(DMSO-d$_6$) 1.26 (d, pyridinium protons adjacent to N$^+$Me), 2.09 (d, pyridinium protons), 3.01 (s, CH.Ph$_2$), 4.88 (d, J 5 Hz, 7—$\underline{H}$), 5.08 (d, J 5 Hz, 6—$\underline{H}$), 5.77 (s, 3—CH$_2$ and N$^+$Me), 6.15 and 6.50 (m, 2—H$_2$).

(b) Diphenylmethyl (6R,7R)-7-[(Z)-2-(2-t-butoxycarbonylprop-2-oxyimino)-2-(2-tritylaminothiazol-4-yl)-acetamido]-3-(1-methylpyridinium-4-yl-thiomethyl)ceph-3-em-4-carboxylate bromide Phosphorus pentachloride (170 mg) in methylene chloride (8 ml) was cooled to 0° C. and the product of Preparation 4 (0.44 g) was added. After stirring for 30 minutes at 0° C. triethylamine (0.25 ml) was added and the solution stirred at 0° for a further 5 minutes before being added over 10 minutes to a stirred solution of the product from Stage (a) (450 mg) in methylene chloride (5 ml) at 0° C. The mixture was stirred at ambient temperature for 2 hours, stored for 16 hours at ca 0° and then poured into a mixture of ethyl acetate (50 ml) and water (50 ml). The mixture was shaken thoroughly and the ethyl acetate layer collected. After evaporation of the organic solvent the solid residue was triturated with a little diethyl ether, filtered, washed with more diethyl ether and dried in vacuo at 40° to yield the title compound (680 mg) as a powder whose nmr spectrum resembled that of the product of Example 5 (b). $\nu_{max}$ (Nujol) 1786 ($\beta$-lactam), 1680 and 1545 (amide, 2600 and 1710 cm$^{-1}$ (CO$_2$H).

(c) (6R,7R)-7-[(Z)-2-(2-Aminothiazol-4-yl)-2-(2-carboxyprop-2-oximino)-acetamido]-3-(1-methylpyridinium-4-ylthiomethyl)ceph-3-em-4-carboxylate The product from Stage (b) (400 mg) was treated with anisole (1 ml) and trifluoroacetic acid (4 ml) for ca 1 hour at 0° and the product isolated substantially as described in Example 5 (c) to yield the title compound whose nmr spectroscopic properties resembled those of the product of Example 3 (b), $\lambda_{max}$ (pH 6 buffer) 230 nm (E$_{1\ cm}^{1\%}$347), 302.5 nm (E$_{1\ cm}^{1\%}$392) and $\lambda_{inf}$ 249.5 nm (E$_{1\ cm}^{1\%}$242).

EXAMPLE 7

(a) Diphenylmethyl (6R,7R)-7-[(Z)-2-(1-t-butoxycarbonylcyclobut-1-oxyimino)-2-(2-tritylaminothiazol-4-yl)acetamido]-3-bromomethylceph-3-em-4-carboxylate Phosphorus pentachloride (9.2 g) in methylene chloride (400 ml) was cooled to −20° C. before the addition of the product of Preparation 6 (23.32 g). The solution was stirred at −20° for ca 30 minutes when triethylamine (12.32 ml.) was added. After a further 5 minutes at −20° the solution was added over 5 minutes to a solution of diphenylmethyl (6R,7R)-7-amino-3-bromomethylceph-3-em-4-carboxylate hydrochloride (19.8 g) and triethylamine (5.6 ml) in methylene chloride (400 ml) maintained at −20° C. After 10 minutes the cooling was removed and the reaction allowed to warm to ambient temperature over ca 30 minutes when it was poured into water (1 l) and methylene chloride (400 ml). The title compound (42 g) was isolated in a similar manner to that described in Example 5 (a). $\tau$(CDCl$_3$) 3.03 (s, C$\underline{H}$ Ph$_2$), 3.24 (s, thiazol-5-yl proton), 4.05 (dd, J 5 Hz+9 Hz, 7—$\underline{H}$), 4.95 (d, J5 Hz, 6—H) 5.72 (s, 3—C$\underline{H}_2$, Br), 6.3–6.7 (broad q, 2—H$_2$), 7.2–8.1 (m, cyclobutyl protons).

(b) Diphenylmethyl (6R,7R)-7-[(Z)-2-(1-t-butoxycarbonylcyclobut-1-oxyimino)-2-(2-tritylaminothiazol-4-yl)acetamido]-3-[1-methylpyridinium-4-ylthiomethyl)ceph-3-em 4-carboxylate bromide The product from Stage (a) (42 g) in tetrahydrofuran (500 ml), was treated with N-methylpyrid-4-thione (5.2 g) and stirred for 3 hours at ambient temperature. After storage for 16 hours at ca 0° the solution was stirred and diethyl ether (2.0 l) added. The solid was filtered off, washed well with diethyl ether and dried at 40° in vacuo to afford the title compound (40.5 g) $\tau(CDCl_3)$ 1.18 (broad s, pyridyl protons adjacent to N+Me), 2.32 (broad s, pyridyl protons adjacent to C—S), 3.05 (s, CHPh$_2$), 3.22 (s, thiazol-5-yl proton) 4.07, (dd, J 5 Hz and 9 Hz, 7—H), 4.88 (d, J 5 Hz 6—H), 5.62 (broad s, 3—CH$_2$ and N+Me), 6.1–6.7 (m, 2—H$_2$) 7.2–8.2 (m, cyclobutylprotons), c) (6R,7R)-7-[(Z)-2-(2-Aminothiazol-4-yl)-2-(1-carboxycyclobut-1-oxyimino)-acetamido]-3-(1-methylpyridinium-4-ylthiomethyl)ceph-3-em-4-carboxylate The product from Stage (a) (40.5 g) was stirred in trifluoroacetic acid (320 ml) and anisole (80 ml) at ca 0° for 1½ hours. The mixture was poured into water (3 l) and diethyl ether (1.5 l). The title compound was isolated as described in Example 5 (c) and had spectroscopic properties resembling those of the product of Example 4 (c). Fluorine assay (ca 4.2%) indicated that the product contained some trifluoroacetic acid.

EXAMPLE 8

(a) Diphenylmethyl (1S,6R,7R)-7-[(Z)-2-(2-t-Butoxycarbonylprop-2-oxyimino)-2-(2-tritylaminothiazol-4-yl)acetamido]-3-[(1-methylpyrimidinium-2-yl)thiomethyl]ceph-3-em-4-carboxylate 1-oxide, bromide The product of Preparation 7 (1.02 g) in dry tetrahydrofuran (10 ml) was treated with 1,2-dihydro-1-methylpyrimidine-2-thione (158 g) and the mixture was stirred at 25° for 1½ hours. The resulting solution was added slowly to stirred ether (150 ml) and the precipitate was filtered off and dried in vacuo to give the title compound (1.043 g) as a solid, $[\alpha]_D+56°$ (c 0.66, CHCl$_3$), $\lambda_{max}$ (EtOH) 364 nm (E$_{1\ cm}^{1\%}$149) with inflections at 240 nm (E$_{1\ cm}^{1\%}$250) and 275 nm (E$_{1\ cm}^{1\%}$140).

(b) Diphenylmethyl (6R,7R)-7-[(Z)-2-(2-t-Butoxycarbonylprop-2-oxyimino)-2-(2-tritylaminothiazol-4-yl)acetamido]-3-[(1-methylpyrimidinium-2-yl)thiomethyl]ceph-3-em-4-carboxylate, iodide The product from Stage (a) (912 mg) in acetone (10 ml) was treated with potassium iodide (525 mg) and the suspension was stirred at 25° for 5 minutes and was then cooled to −10°. Acetyl chloride (0.115 ml) was added and the mixture was stirred at 0° to +2° for 50 minutes. The mixture was then added to a stirred solution of sodium metabisulphite (600 mg) in water (60 ml). The precipitate was filtered off and washed with water and dried in vacuo over phosphorus pentoxide to give a solid (880 mg). A solution of the solid in acetone (5 ml) was treated with potassium iodide (525 mg) and cooled to −10° and then treated with acetyl chloride (0.115 ml). The mixture was stirred at 0° to +2° for 40 minutes, and was then added to a stirred solution of sodium metabisulphite (1 g) in water (60 ml). The precipitate was filtered off and washed with water and dried in vacuo over phosphorus pentoxide to give the title compound (940 mg) as a solid, m.p. 142° to 156° (decomp), $[\alpha]_D−67°$ (c 0.45, acetone).

(c) (6R,7R)-7-[(Z)-2-(2-Aminothiazol-4-yl)-2-(2-carboxyprop-2-oxyimino)acetamido]-3-[(1-methylpyrimidinium-2-yl)thiomethyl]-ceph-3-em-4-carboxylate, trifluoroacetate The product from Stage (b) (800 mg) was wetted with anisole (0.5 ml) and treated with trifluoroacetic acid (2 ml). The mixture was swirled at 24° for 2½ minutes, and was then evaporated to an oil which was triturated with ether. The solid (560 mg) was filtered off and washed with ether and dried in vacuo. It was then treated with anisole (0.14 ml) and trifluoroacetic acid (16 ml) at 24° for 15 minutes. The mixture was filtered and the residue was washed with trifluoroacetic acid (5 ml). The combined filtrates were evaporated to an oil which was triturated with ether. The solid was filtered off and washed with ether and dried in vacuo to give the title compound (409 mg) as a solid, $[\alpha]_D−45°$ (c 0.53, H$_2$O:EtOH=1:1), $\lambda_{max}$ (pH 6 buffer) 253 nm (E$_{1\ cm}^{1\%}$297) with an inflection at 291 nm (E$_{1\ cm}^{1\%}$181).

EXAMPLE 9

(6R,7R)-7-[(Z)-2-(2-Aminothiazol-4-yl)-2-(2-carboxyprop-2-oxyimino)-acetamido]-3-[(1,2-dimethylpyrazolium-3-yl)thiomethyl]ceph-3-em-4-carboxylate, sodium salt The product of Example 3 (a) (264 mg) and sodium bicarbonate (135 mg) were warmed with water (0.3 ml) until a solution had formed. 1,2-Dimethylpyrazol-4-ine-3-thione (97 mg), sodium iodide (450 mg), and water (0.1 ml) were added, and the mixture was heated at 70° for 4 hours with occasional swirling. The mixture was then allowed to cool and was diluted with water (0.5 ml) and was added slowly to stirred acetone (100 ml). The precipitate was filtered off and washed with acetone and with ether and dried in vacuo to give a solid (318 mg). The solid (282 mg) was dissolved in a little water and passed through a column of 'Amberlite' XAD-2 (100 g). Elution was with water (66 ml. fractions: 1 to 6) and then water:ethanol=3:1 (66 ml. fractions: 7 to 12). Fractions 7 to 10 were combined and evaporated to ca. 150 ml and freeze-dried to a white foam (158 mg) which was triturated with ether to give the title compound (133 mg) as a white solid, $[\alpha]_D−16°$ (c 0.21, water), $\lambda_{max}$ (pH 6 buffer) 234 nm (E$_{1\ cm}^{1\%}$302) with an inflection at 256 nm (E$_{1\ cm}^{1\%}$255).

EXAMPLE 10

(a) Diphenylmethyl(1S,6R,7R)-7-[(Z)-2-(2-t-Butoxycarbonylprop-2-oxyimino)-2-(2-tritylaminothiazol-4-yl)acetamido]-3-(pyrid-3-ylthiomethyl)ceph-3-em-4-carboxylate, 1-oxide A mixture of the product from Preparation 7 (1.54 g) and 3-mercaptopyridine (0.200 g) in dry tetrahydrofuran (12 ml) was treated with triethylamine (0.224 ml). The grey suspension was stirred for 10 minutes at 22° then partitioned between water (150 ml) and ethyl acetate (150 ml).

The organic phase was washed with water (2×50 ml) and then dried and evaporated to give a foam (1.546 g).

This foam was purified by chromatography on a column of silica (Merck Kieselgel 60, 70–230 mesh, 50 g) eluted with toluene-ethyl acetate (2:1).

Appropriate fractions were collected and evaporated to give the title compound (1.385 g) as a foam, $[\alpha]_D+23°$ (c 0.81, CHCl$_3$), and $\nu_{max}$ (CHBr$_3$) 3390 (NH), 1804 ($\beta$-lactam), 1725 cm$^{-1}$ (CO$_2$R).

(b)
Diphenylmethyl(1S,6R,7R)-7-[(Z)-2-(2-t-Butoxycarbonylprop-2-oxyimino)-2-(2-tritylaminothiazol-4-yl)acetamido]-3-[(1-methylpyridinium-3-yl)thiomethyl]ceph-3-em-4-carboxylate, 1-oxide, Iodide Salt The product from Stage (a) (1.28 g) and indomethane (5 ml) was allowed to stand at 22° for 1¼ hours, then ether (50 ml) was added. The precipitate was triturated and filtered off and washed with ether and dried in vacuo to give the title compound (1.30 g) as a solid, $[\alpha]_D+21°$ (c 0.29, CHCl$_3$), and $\nu_{max}$ (Nujol) 3380 (NH), 1800 ($\beta$-lactam), 1730 cm$^{-1}$ (CO$_2$R).

(c)
Diphenylmethyl(6R,7R)-7-[(Z)-2-(2-t-Butoxycarbonylprop-2-oxyimino)-2-(2-tritylaminothiazol-4-yl)acetamido]-3-[(1-methylpyridinium-3-yl)thiomethyl]ceph-3-em-4-carboxylate, Iodide Salt A solution of the product from Stage (b) (1.18 g) in acetone (5 ml) was treated with potassium iodide (0.665 g) and then cooled to −10° and stirred and treated with acetyl chloride (0.143 ml). The mixture was stirred at 0° to +2° for 30 minutes after which more acetone (5 ml) was added. After a further 30 minutes at 0° to +2° the mixture was diluted with a solution of sodium metabisulphite (0.6 g) in water (60 ml) and the precipitate was triturated to a solid which was filtered off, washed with water and dried in vacuo to give a solid (1.3 g).

The product was partitioned between chloroform (containing some ethyl acetate) and dilute aqueous sodium metabisulphite solution. The organic layer was washed with water (twice) and dried and evaporated to a foam (1.194 g).

A solution of this product (ca 1.19 g) in N,N-dimethylformamide (5 ml) was stirred with potassium iodide (0.665 g) at 22° for 15 minutes and then the mixture was cooled to −10° and treated with acetyl chloride (0.15 ml). The solution was stirred at 0° to +2° for 1 hour and was then added slowly to a stirred solution of sodium metabisulphite (1 g) in water (100 ml). The precipitate was filtered off and washed with water. It was then partitioned between chloroform and dilute sodium metabisulphite solution. The organic layer was washed with water (twice) and brine then dried and evaporated to give the title compound (1.137 g) as a foam; $[\alpha]_D+8°$ (c 0.5, CHCl$_3$), and $\nu_{max}$ (CHBr$_3$), 3405 and 3275 (NH), 1793 ($\beta$-lactam), 1725 (CO$_2$R), 1684 and 1527 (CONH), 1624 (C=N) and 758 cm$^{-1}$ (phenyl).

(d)
(6R,7R)-7-[(Z)-2-(2-Aminothiazol-4-yl)-2-(2-carboxyprop-2-oxyimino)acetamido]-3-[(1-methylpyridinium-3-yl)thiometyl]-ceph-3-em-4-carboxylic acid, Trifluoroacetate Salt The product of Stage (c) (0.99 g) was treated with anisole (1 ml) and trifluoroacetic acid (4 ml) as described in Example 8 (c) to give the title compound (0.583 g) as a solid, $[\alpha]_D+27°$ (c 0.69, H$_2$O:EtOH=1:1), $\lambda_{max}$ (pH 6 buffer) 232 nm (E$_1$ $_{cm}$$^{1\%}$286) and 256 nm (E$_1$ $_{cm}$$^{1\%}$254).

EXAMPLE 11

(a)
Diphenylmethyl(1S,6R,7R)-7-[(Z)-2-(2-t-Butoxycarbonylprop-2-oxyimino)-2-(2-tritylaminothiazol-4-yl)acetamido]-3-[1,3-dimethylimidazolium-2-yl)thiomethyl]ceph-3-em-4-carboxylate, 1-Oxide, Bromide Salt The product of Preparation 7 (0.825 g) in dry tetrahydrofuran (4 ml) was treated with 1,3-dimethylimidazol-4-ine-2-thione (0.108 g) and the mixture was stirred at 24° for 3 hours. The resulting solution was added to stirred ether (150 ml) and the precipitate was filtered off and dried in vacuo to give the title compound (0.834 g) as a solid, m.p. 150° to 160° (decomp); $[\alpha]_D+19°$ (c 0.78, CHCl$_3$).

(b)
Diphenylmethyl(6R,7R)-7-[(Z)-2-(2-t-Butoxycarbonylprop-2-oxyimino)-2-(2-tritylaminothiazol-4-yl)acetamido]-3-[(1,3-dimethylimidazlium-2-yl)thiomethyl]ceph-3-em-4-carboxylate, Iodide Salt The product obtained in Stage (a) (0.725 g) in acetone (5 ml) was treated substantially as described in Example 8 (b) to give the title compound (0.759 g) as a solid, m.p. 135° to 145° (decomp.); $[\alpha]_D+10°$ (C 0.29, CHCl$_3$).

(c)
(6R,7R)-7-[(Z)-2-(2-Aminothiazol-4-yl)-2-(2-carboxyprop-2-oxyimino)acetamido]-3-[(1,3-dimethylimidazolium-2-yl)thiomethyl]ceph-3-em-4-carboxylic Acid, Trifluoroacetate Salt The product obtained from Stage (b) (0.65 g) was treated with anisole (0.5 ml) and treated with trifluoroacetic acid (2 ml) and the product isolated substantially as described in Example 8 (c) to give the title compound (0.273 g) as a solid $[\alpha]_D+110°$ (c 0.52, EtOH:H$_2$O=1:1); $\lambda_{max}$ (pH 6 buffer) 235 nm (E$_1$ $_{cm}$$^{1\%}$307), $\lambda_{inf}$253 nm (E$_1$ $_{cm}$$^{1\%}$245), $\lambda_{inf}$275 nm (E$_1$ $_{cm}$$^{1\%}$194).

EXAMPLE 12

(a)
(6R,7R)-7-[(Z)-2-(2-Aminothiazol-4-yl)-2-(1-carboxycyclobut-1-oxyimino)-acetamido]-3-(pyrid-4-yl-thiometyl)ceph-3-em-4-carboxylate The product of Example 2 (b) (12 g) was added to a solution of sodium iodide (21 g) in water (20 ml) at ambient temperature. Sodium bicarbonate (3.72 g) was then added over 40 minutes. 4-Mercapto-pyridine (3.5 g) was then added and the reaction mixture heated to 70° C. for 4 hours. The mixture was then cooled to ambient temperature and added to acetone (2 l) to give a solid (14 g) containing the title compound. $\tau$(DMSO-d$_6$) includes:—3.24 (s, aminothiazole proton), 1.69 (d, J=5 Hz)+2.68 (d, J=5 Hz) (pyridinium protons), 4.2–4.5 (m, 7—H), 4.98, 7.2–7.8, +7.8–8.4 (m, cyclobutane proton).

(b)
(6R,7R)-7-[(Z)-2-(2-Aminothiazol-4-yl)-2-(1-carboxycyclobut-1-oxyimino)-acetamido]-3-(1-methylpyridinium-4-yl-thiomethyl)ceph-3-em-4-carboxylate The solid from Stage (a) (5 g) was dissolved in methanol (30 ml) and water (20 ml) at ambient temperature. A solution of methyl iodide (0.84 g) in methanol (10 ml) was then added. After 24 hours at ambient temperature, the solvent was removed and the residue triturated with acetone to give a solid (3.98 g) containing the title compound. τ(DMSO-d$_6$) includes:—5.84 (s, methyl group protons on pyridinium ring).

Analysis by high pressure liquid chromatography gave a peak having a retention time identical to that of the product of Example 4 (c).

EXAMPLE 13

(a)

Diphenylmethyl(6R,7R)-7-[(Z)-2-(1-t-butoxycarbonyl-cyclobut-1-oxyimino)-2-(2-tritylaminothiazol-4-yl)acetamido]-3-(1-methylpyridinium-4-ylthiomethyl)-ceph-3-em-4-carboxylate Bromide Phosphorus pentachloride (0.92 g) in methylene chloride (50 ml) was cooled to 0° C. and the product of Preparation 6 (2.33 g), was added. The solution was stirred at ca. −20° for 30 minutes when triethylamine (1.25 ml) was added. After a further 5 minutes at −20°, the solution was added to a stirred suspension of the product of Example 6 (a) in methylene chloride (40 ml) at −10°. The mixture was stirred at ambient temperature for ca. 2 hours and became almost clear before being poured into water (200 ml) and ethyl acetate (300 ml). The mixture was shaken and the ethyl acetate layer separated. After evaporation of the solvent in vacuo, the solid residue was dissolved in tetrahydrofuran (30 ml) and treated with diethyl ether (90 ml). The solid that precipitated was filtered, washed with diethyl ether and dried in vacuo at 40° to yield the title compound (2.3 g) as a powder, whose spectroscopic properties resembled those of the product of Example 7 (b).

(b)

(6R,7R)-7-[(Z)-2-(2-Aminothiazol-4-yl)-2-(1-carboxycyclobut-1-oxyimino)-acetamido]-3-(1-methylpyridinium-4-ylthiomethyl)ceph-3-em-4-carboxylate The product from Stage (a) (0.9 g) was stirred in 98% formic acid (7 ml) for 15 minutes at room temperature before conc. hydrochloric acid (0.2 ml) was added and stirring continued for a total of 1½ hours. The solvent was evaporated under high vacuum at room temperature and the resultant solid foam triturated with acetone (30 ml). The solid was filtered, washed with diethyl ether and dried in vacuo to afford the title compound (0.5 g) whose nmr spectrum resembled that of the product of Example 4 (c) as a powder. λ$_{max}$(pH 6 buffer) 226 nm (E$_{1 cm}$$^{1\%}$286), 303.5 nm (E$_{1 cm}$$^{1\%}$346) and λ$_{inf}$255 nm (E$_{1 cm}$$^{1\%}$215).

PHARMACY EXAMPLES

EXAMPLE A

Dry Powder for Injection

Formula Per Vial (6R,7R)-7-[(Z)-2-(2-Aminothiazol-4-yl)-2-(2-carboxy-prop-2-oxyimino)acetamido]-3-(1-methylpyridinium-4-yl)thiomethylceph-3-em-4-carboxylate: 500 mg
Sodium acetate, anhydrous: 69 mg Method The cephalosporin antibiotic was blended with sodium acetate and filled into a glass vial. The vial headspace was purged with nitrogen and a combination seal applied by crimping. The product was dissolved, as for administration, by the addition of 2 ml Water for Injections.

EXAMPLE B

Intramammary Injection (Veterinary)

Formula

| | |
|---|---|
| (6R,7R)-7-[(Z)—2-Aminothiazol-4-yl)-2-(2-carboxy-prop-2-oxyimino)acetamido]-3-(1-methylpyridinium-4-yl)thiomethylceph-3-em-4-carboxylate, monosodium salt | 200 mg |
| Polysorbate 60 3.0% w/v <br> White beeswax 6.0% w/v <br> Arachis Oil 91.0% w/v | to 5.0 g |

Method

Heat the last three ingredients together at 150° C. for one hour and then cool to room temperature with stirring. Add the sterile milled antibiotic aseptically to this vehicle and refine with a high speed mixer. Fill the product aseptically into sterile plstic styringes, using a fill weight of 5.00 g per container.

EXAMPLE C

Dry Powder for Injection

Formula Per Vial (6R,7R)-7-[(Z)-2-(2-Aminothiazol-4-yl)-2-(1-carboxycyclobut-1-oxyimino)acetamido]-3-(1-methylpyridinium-4-yl)thiomethylceph-3-em-4-carboxylate: 500 mg
Meglumine: 161 mg Method The cephalosporin antibiotic was blended with megluimine and filled into a glass vial. The vial headspace was purged with nitrogen and a combination seal applied by crimping. The product was dissolved, as for administration, by the addition of 2 ml Water for Injections.

EXAMPLE D

Dry Powder for Injection

Fill the sterile (6R,7R)-7-[(Z)-2-(2-aminothiazol-4-yl)-2-(1-carboxycyclobut-1-oxyimino)acetamido]-3-(1-methylpyridinium-4-yl)thiomethylceph-3-em-4-carboxylate, monosodium salt into glass vials such that each vial contains an amount equivalent to 1.00 g of the antibiotic acid. Carry out the filling aseptically under a blanket of sterile nitrogen. Close the vials using rubber disks or plugs, held in position by aluminum overseals, thereby preventing gaseous exchange or ingress of microorganisms. Reconstitute the product by dissolving in Water for Injections or other suitable sterile vehicle shortly before administration.

Polysorbate 60 is a polyoxyethylene sorbitan monostearate containing about 20 ethylene oxide units and meglumine is N-Methylglucamine BP.

We claim:

1. A cephalosporin antibiotic selected from the group consisting of compounds of the formula:

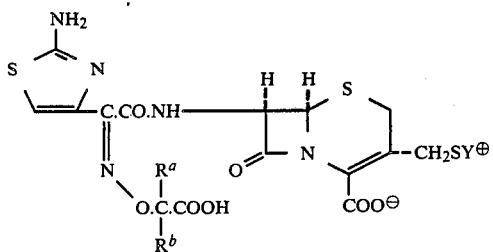

(I)

wherein $R^a$ and $R^b$, which may be the same or different, each represent a $C_{1-4}$ alkyl group or $R^a$ and $R^b$ together with the carbon atom to which they are attached form a $C_{3-7}$ cycloalkylidene group and $Y^\oplus$ represents a C-linked pyridinium ring wherein the quaternary nitrogen is substituted by a $C_{1-4}$ alkyl group and non-toxic salts thereof.

2. A compound as claimed in claim 1 wherein $R^a$ and $R^b$ each represents a methyl group.

3. A compound as claimed in claim 1 wherein $R^a$ and $R^b$ together with the carbon atom to which they are attached form a $C_{3-5}$ cycloalkylidene group.

4. A cephalosporin antibiotic selected from the group consisting of compounds of the formula

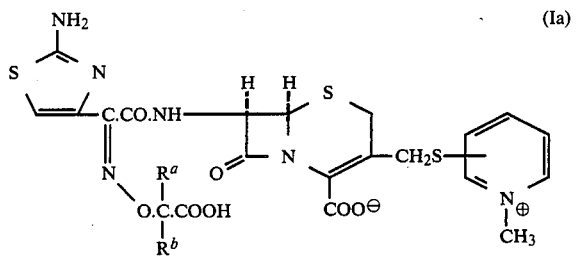

(Ia)

wherein $R^a$ and $R^b$, which may be the same or different, each represent a $C_{1-4}$ alkyl group or $R^a$ and $R^b$ together with the carbon atom to which they are attached form a $C_{3-7}$ cycloalkylidene group and non-toxic salts thereof.

5. A compound as claimed in claim 4 which is (6R,7R)-7-[(Z)-2-(2-aminothiazol-4-yl)-2-(1-carboxycyclobut-1-oxyimino)acetamido]-3-[(1-methylpyridinium-4-yl)thiomethyl]ceph-3-em-4-carboxylate.

6. A non-toxic salt of the compound as claimed in claim 5.

7. The mono-sodium salt of the compound as claimed in claim 5.

8. A compound as claimed in claim 4 which is (6R,7R)-7-[(Z)-2-(2-aminothizol-4-yl)-2-(2-caroxyprop-2-oxyimino)acetamido]-3-[(1-methylpyridinium-4-yl)thiomethyl]ceph-3-em-4-carboxylate or a non-toxic salt thereof.

9. A compound as claimed in claim 4 which is (6R,7R)-7-[(Z)-2-(2-aminothiazol-4-yl)-2-(2-carboxyprop-2-oxyimino)acetamido]-3-[(1-methylpyridinium-2-yl)thiomethyl]ceph-3-em-4-carboxylate or a non-toxic salt thereof.

10. A compound as claimed in claim 4 which is (6R,7R)-7-[(Z)-2-(2-aminothiazol-4-yl)-2-(1-carboxycyclobut-1-oxyimino)acetamido]-3-[(1-methylpyridinium-2-yl)thiomethyl]ceph-3-em-4-carboxylate or a non-toxic salt thereof.

11. A compound as claimed in claim 4 which is (6R,7R)-7-[(Z)-2-(2-aminothiazol-4-yl)-2-(2-carboxyprop-2-oxyimino)acetamido]-3-[(1-methylpyridinium-3-yl)thiomethyl]ceph-3-em-4-carboxylate or a non-toxic salt thereof.

12. A pharmaceutical compositions for use in human or veterinary medicine comprising an effective amount of an antibiotic compound as claimed in claim 1 in association with a pharmaceutical carrier or excipient.

13. A method of combatting a bacterial infection in a human or an animal comprising administering an antibacterially effective amount of a compound as claimed in claim 1.

* * * * *